United States Patent
Ning et al.

[11] Patent Number: 5,903,343
[45] Date of Patent: May 11, 1999

[54] METHOD FOR DETECTING UNDER-ETCHED VIAS

[75] Inventors: Xian J. Ning, Mohegan Lake; Rainer Florian Schnabel, Wappingers Falls, both of N.Y.

[73] Assignee: Siemens Aktiengesellschaft, Munich, Germany

[21] Appl. No.: 08/997,460

[22] Filed: Dec. 23, 1997

[51] Int. Cl.$^6$ .................................................. G01N 21/84
[52] U.S. Cl. ................................. 356/241.1; 356/237.1; 356/445
[58] Field of Search ............................. 356/241.1, 237.1, 356/445, 446, 447, 448

[56] References Cited

U.S. PATENT DOCUMENTS 5,214,283  5/1993  Le ............................................ 250/307
5,301,012  4/1994  King et al. ............................... 356/237

*Primary Examiner*—Richard A. Rosenberger
*Attorney, Agent, or Firm*—Stanton C. Braden

[57] ABSTRACT

Methods for detecting under-etched vias, spaces, or under-polished portions in a wafer stack are disclosed. The wafer stack comprises a dielectric layer disposed on a metal layer. The dielectric layer has a plurality of vias etched therein. The wafer stack, including the plurality of vias, is exposed to an etchant which is configured to etch the metal layer at a substantially faster rate than the dielectric layer. As a result, cavities are formed in the metal layer below properly-etched vias. Then, the vias in the wafer stack are optically inspected to detect and identify under-etched vias, which reflect more light than the cavities etched into the metal layer.

29 Claims, 4 Drawing Sheets

METHOD FOR DETECTING UNDER-ETCHED VIAS

BACKGROUND OF THE INVENTION

The present invention relates to the fabrication of semiconductor integrated circuits (ICs). More particularly, the present invention relates to methods for inspecting under-etched vias.

In semiconductor IC fabrication, devices such as component transistors are formed on a semiconductor wafer or substrate, which is typically made of silicon. Successive layers of various materials may be deposited onto the wafer or substrate to form a layer stack. Very large scale integration (VLSI) chips often require more than a single level of metal to provide sufficient interconnection capability. Semiconductor IC fabrication processes typically use vias to interconnect multi-layer metal levels. During the fabrication process, the vias are usually etched or drilled through the dielectric or insulator layer.

Unfortunately however, etching or forming vias through the dielectric or insulator layer often does not result in completely etched vias. As an example, Prior Art FIG. 1 illustrates a cross section of a silicon wafer stack 100 having a plurality of vias 110, 112, 114, 116, 118, and 120. Wafer stack 100 comprises a wafer 102, an oxide layer 104, a metal layer 106, and a dielectric layer 108 having vias 110 through 120. As shown in FIG. 1, vias 110, 114, 116, and 120 do not come in direct contact with metal layer 106. Vias 110, 114, 116, and 120 are commonly referred to as "under-etched" vias since they have not been etched completely through dielectric layer 108. These under-etched vias may cause an open circuit by preventing electrical contact between an upper metal layer which may be subsequently deposited above dielectric layer 108 and lower metal layer 106. On the other hand, vias 112 and 118 are properly etched because they have been etched completely through dielectric layer 108. Since vias 112 and 118 come in direct contact with metal layer 106, no open circuit results between an upper metal layer and lower metal layer 106. Those skilled in the art will appreciate that layers 104, 106, and 108 can be disposed on wafer 102 in a different order and that the vias can be formed on any one of layers 104, 106, and 108.

It should also be noted that the silicon wafer layer stack 100 of Prior Art FIG. 1 is shown for illustration purposes only and other additional layers, which have not been described, may be present above, below, and between the layers shown. These other layers may be used to provide, for example, additional interconnecting layers or layers from which components may be formed. Further, not all of the shown layers need necessarily be present and some or all may be substituted by other different layers.

In the past, detecting the under-etched vias has presented problems due to the size and number of vias in a wafer, which can number into millions in a single chip using sub-micron technology. Several conventional methods have been devised to detect under-etched vias in a wafer stack. One method uses a scanning electron microscope (SEM) to look at a cross section of a wafer. Specifically, the wafer is broken at the cross section. The SEM is then used to look at the vias along the cut cross section of the wafer. However, the SEM method has several drawbacks. First, the SEM equipment is typically very expensive. Second, cutting the wafer through the cross section requires non-trivial preparation, which is time consuming. Finally, the observable vias through the cut cross section is small compared to the number of vias on the entire wafer, which may run into millions.

Another prior art method utilizes a profilometer to check for the under-etched vias. The profilometer is basically a needle which follows the contour of a wafer. Unfortunately, the profilometer cannot be used on a regular wafer featuring, for example, the 0.25 or sub −0.25 micron technology. Instead, a much larger test structure must be created to use the profilometer. This larger test structure does not accurately reflect the features of the regular wafer sample. For example, the etch rates can differ significantly between the regular wafer sample and the larger test structure.

In addition, a traditional method used an equipment called "atomic force microscope" (AFM) to check for the under-etched vias. Specifically, the AFM probed a needle into the vias to check whether the needle sensed a metal or a dielectric. The method using AFM has several drawbacks. First, the AFM equipment is very expensive. Second, it can detect only a limited number of vias. Finally, the AFM equipment is difficult to operate because the mechanical needle must actually be inserted into a via.

In view of the foregoing, what is desired is improved methods for detecting under-etched vias in a wafer stack.

SUMMARY OF THE INVENTION

The present invention provides a method for identifying under-etched vias, spaces, or under-polished portions in a wafer stack. In one embodiment, the wafer stack comprises a dielectric layer disposed on a metal layer. The dielectric layer has a plurality of vias etched therein. The wafer stack, including the plurality of vias, is exposed to an etchant which is configured to etch the metal layer at a substantially faster rate than the dielectric layer. As a result, cavities are formed in the metal layer below properly-etched vias. Then, the vias in the wafer stack are optically inspected to detect and identify under-etched vias which reflect more light than the cavities etched into the metal layer.

In another embodiment, a wafer stack comprises a metal layer disposed on a dielectric layer. The metal layer has a plurality of spaces etched therein. The wafer stack, including the plurality of vias, is exposed to an etchant which is configured to etch the dielectric layer at a substantially faster rate than the metal layer. As a result, cavities are formed in the dielectric layer below properly-etched spaces of the plurality of spaces. The vias in the wafer stack are then optically examined to detect and identify under-etched spaces, which reflect more light than the cavities etched into the dielectric layer.

In yet another embodiment, a wafer stack comprises a polished metal layer disposed over a dielectric layer. The dielectric layer forms a structure having a plurality of portions. The wafer stack, including the plurality of portions, is exposed to an etchant which selectively etches the dielectric layer without substantially etching the metal in the metal layer. As a result, cavities are formed in the dielectric layer below properly-polished portions. The plurality of portions are then optically inspected to detect and identify under-polished metal portions which reflect more light than the cavities etched into the dielectric layer.

BRIEF DESCRIPTION OF THE DRAWINGS

The features of the present invention may best be understood by reference to the following description of the presently preferred embodiments together with the accompanying drawings.

Prior Art

DETAILED DESCRIPTION OF THE INVENTION

An invention is described for providing a method for identifying under-etched vias, spaces, or under-polished portions in a wafer stack with savings in cost and complexity. In the following description, numerous specific details are set forth in order to provide a thorough understanding of the present invention. It will be obvious, however, to one skilled in the art, that the present invention may be practiced without some or all of these specific details. In other instances, well known process steps have not been described in detail in order not to unnecessarily obscure the present invention.

The present invention provides methods for detecting under-etched vias, spaces, or under-polished portions in a wafer stack. In one aspect of the present invention, the under-etched vias formed in a dielectric layer disposed above a metal layer are detected by first etching the wafer stack with an etchant that selectively etches the underlying metal layer without substantially etching the dielectric material. Thereafter, the wafer stack is optically inspected to ascertain the presence and density of the under-etched vias.

In another embodiment of the present invention, the under-etched lines formed in a metal layer disposed above a dielectric layer are detected by first etching the wafer stack with an etchant that selectively etches the underlying dielectric layer without substantially etching the metal. Subsequently, the wafer stack is optically examined to detect and identify the under-etched metal lines.

In yet another embodiment, the present invention detects, after chemical-mechanical polish (CMP), under-polished metal layer portions in a wafer structure comprising a metal layer disposed over a damascene dielectric layer structure. The dielectric layer is exposed to an etchant which selectively etches the oxide layer without substantially etching the metal in the metal layer to enhance the contrast. Thereafter, the wafer stack is optically inspected to ascertain the presence and density of the under-polished metal layer portions and/or the over-polished dielectric layer portions.

Figure 1:
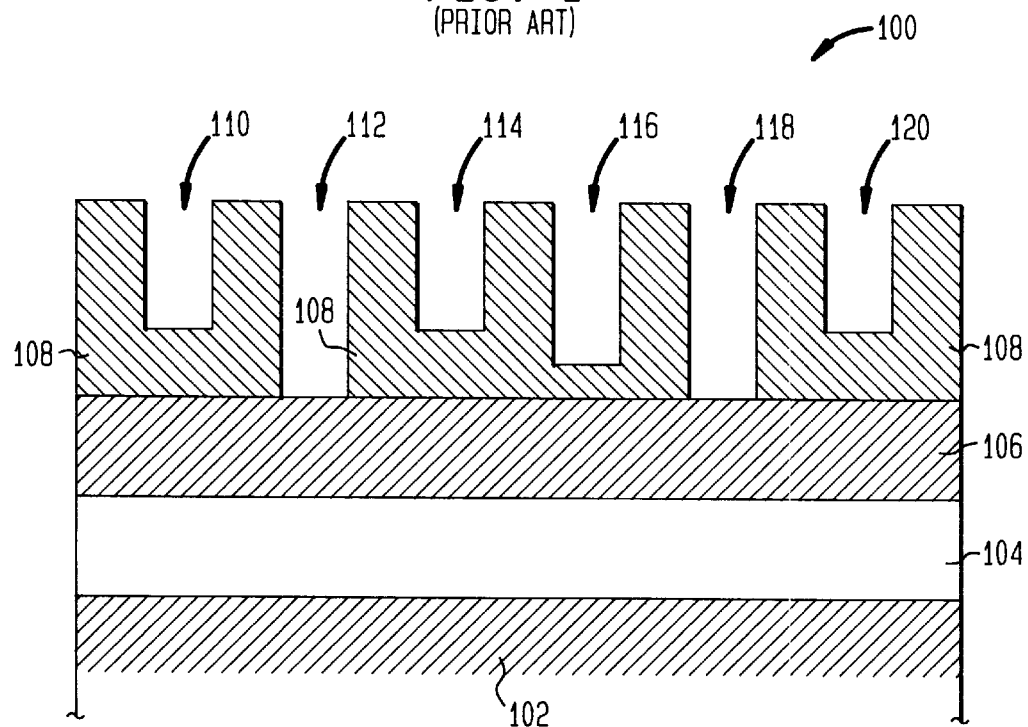
FIG. 1 illustrates a cross section of a silicon wafer stack having a plurality of vias.
Figure 2:
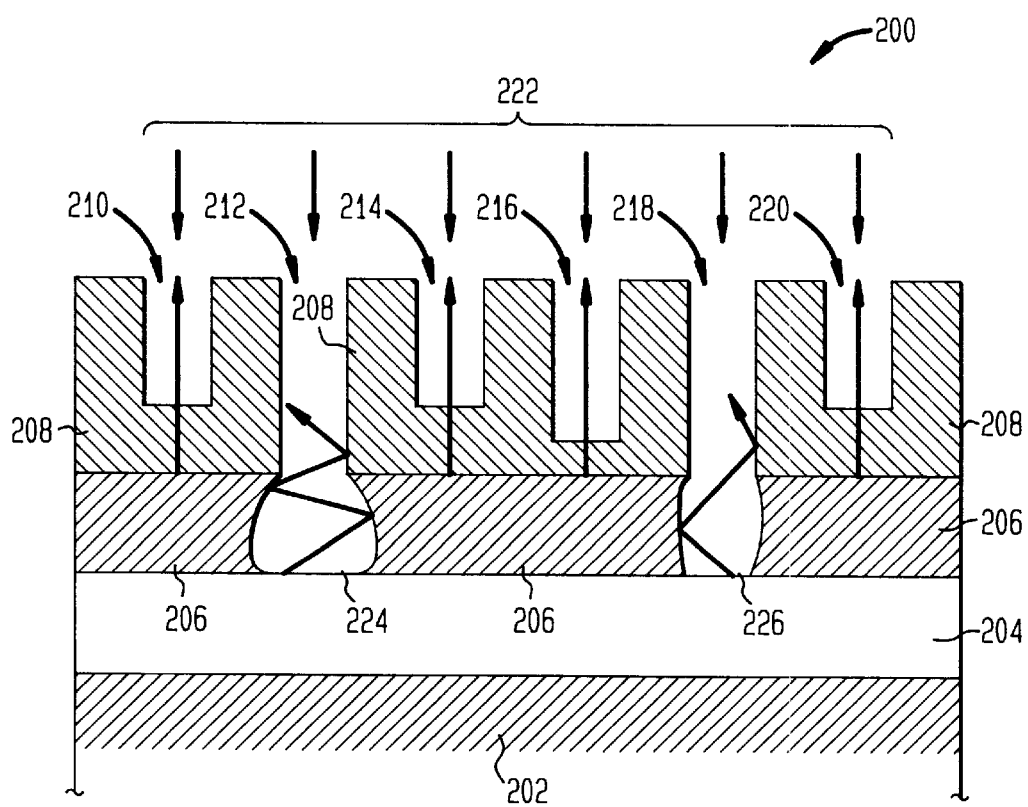
FIG. 2 illustrates in accordance with one aspect of the present invention a cross section of the wafer stack after being exposed to an etchant that selectively etches the underlying metal material without substantially etching the dielectric material.

To facilitate discussion, FIG. 2 illustrates a cross section of wafer stack 200 after being exposed to an etchant that selectively etches the underlying metal material without substantially etching the dielectric material. The wafer stack 200 includes a plurality of vias 210, 212, 214, 216, 218, and 220 etched in a dielectric layer 208 disposed on top of a conductive layer 206. The conductive layer comprises, for example, metal. In this configuration, vias 210, 214, 216, and 220 have been under-etched since some dielectric material of dielectric layer 208 lies between the vias 210, 214, 216, and 220 and metal layer 206.

In contrast, vias 212 and 218 have been properly etched through dielectric layer 208. The etchant is preferably chosen to have high selectivity of metal layer 206 to dielectric layer 208. That is, the etchant etches metal layer 206 at a substantially faster rate than dielectric layer 208. As a result, the etchant creates holes or cavities 224 and 226 in conductive layer 206 under properly-etched vias 212 and 218, respectively. In contrast, dielectric layer 208 inhibits the etchant from etching conductive layer 206 underneath under-etched vias 210, 214, 216, and 220. Thus, holes or cavities are typically not formed in metal layer 206 below under-etched vias 210, 214, 216, and 220. In the present invention, the conductive layer comprises metal such as tungsten (W), aluminum (Al), and copper (Cu). Even though such metals are employed in the present invention, other metals can also be utilized in the present invention to provide a conductive layer. The suitable etchants for these metals that are selective are well known in the art and include, for example, HCl and HCl-based solutions, NaOH and NaOH-based solutions, phosphoric acid and phosphoric-acid based solutions, acetic acid, nitride acid, etc. The dielectric materials employed in dielectric layer 208 are also well known in the art and include any silicon oxide based materials such as TEOS (undoped silicate glass), BPSG (boron-phosphorous doped silicate glass), PSG (p-doped silicate glass), NSG (n-doped silicate glass), SOG (spin-on-glass), hydrogen silsesquioxane SOG (e.g., Dow Corning's Fox), etc.

With reference to FIG. 2, upon exposure to light 222, which may be ambient light or light from a provided light source, vias 210, 212, 214, 216, 218, and 220 reflect back varying amount of light depending on the presence and size of holes or cavities underneath. For example, a hole or cavity etched in metal layer 206 underneath a via will scatter incoming light to a greater extent than the flat, unetched metal surface underneath the under-etched vias.

In contrast, the flat, unetched metal surface underneath under-etched vias 210, 214, 216, and 220 tends to scatter less light and therefore will reflect more light through. Hence, the light reflected back from under-etched vias 210, 214, 216, and 220 appears brighter than light reflected back from holes or cavities 224 and 226. Conversely, holes or cavities 224 and 226 reflect back less light due to scattering and hence appear darker than under-etched vias 210, 214, 216, and 220.

In one embodiment, the present invention employs an optical microscope equipment to identify under-etched vias and properly etched vias. Some exemplary optical microscope equipment suitable for examining a whole wafer to determine the location and statistic of yield (i.e., percentage of defects) are KLA 2135 and KLA-Tencor AIT ("KLA equipment"), both manufactured by KLA-Tencor of San Jose, Calif. The KLA equipment exposes the vias in the wafer stack to light and identifies the brighter vias as the under-etched vias and the darker vias as the properly-etched vias. Specifically, the KLA equipment takes two shots of the wafer stack including the vias before and after the etching process and stores the images digitally in memory. The KLA equipment then compares the light contrast in the two snapshots and identifies the under-etched vias and properly-etched vias. Although the present invention utilizes the above mentioned KLA equipment, the present invention may be practiced with any optical microscope equipment with resolutions to distinguish vias in a wafer stack.

Figure 3:
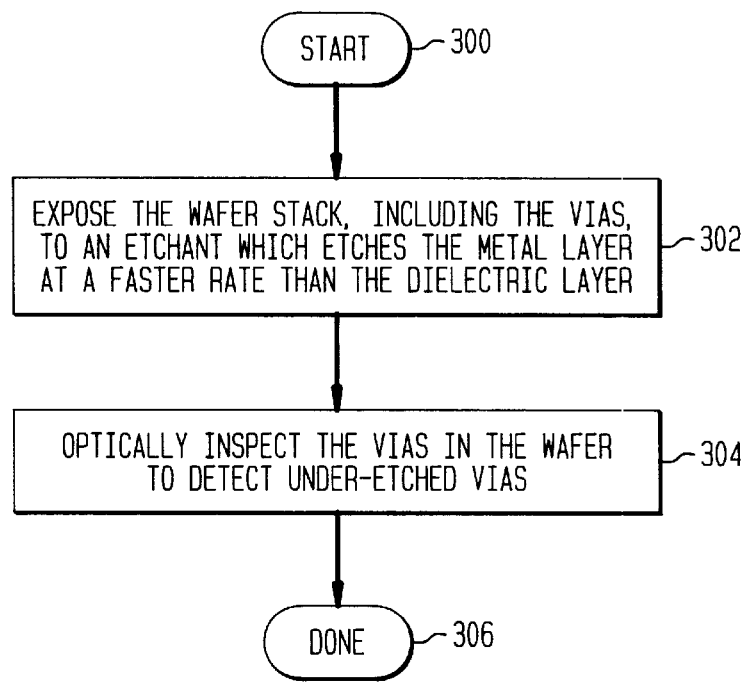
FIG. 3 illustrates in accordance with one embodiment of the present invention the steps involved in detecting under-etched vias among the plurality of vias etched in the wafer stack.

FIG. 3 illustrates the steps involved in detecting under-etched vias among the plurality of vias etched in wafer stack 200. In step 302, the wafer stack including vias is exposed to an etchant. Preferably, the etchant is characterized by an etch rate selectivity, or simply selectivity, which etches the conductive layer at a substantially faster rate than it etches the dielectric layer so that the dielectric layer is not substantially etched by the etchant. In short, the preferred etchant exhibits a high metal to dielectric selectivity. During the etching process, the properly-etched vias allow the etchant to come in direct contact with the metal layer and etch a hole or a cavity in the metal layer. In contrast, the dielectric layer underneath the under-etched vias forms a barrier to the etchant so that the etchant is inhibited from reaching the metal layer underneath the dielectric layer in the under-etched vias. The wafer stack is thus exposed to the etchant until the metal layer underneath the properly etched vias has been etched to a desired thickness. After the etching process, the wafer stack can be cleaned and/or dried.

The preferred etching method of the present invention is a wet etching process where the wafer stack is exposed, for example by dipping or bathing, to an etching solution such as hydrochloric acid (HCl). Even though the preferred etching technique is wet etching, those skilled in the art will recognize that other etching techniques that can selectively etch the metal layer can be used such as dry etching, plasma etching, etc.

Then in step 304, the wafer stack is optically inspected to detect and identify under-etched vias and properly etched vias. When the vias of the wafer stack are exposed to light, the metal layer underneath the under-etched vias reflect back much of the light through the vias. On the other hand, the walls defining the holes or cavities formed in the metal layer scatter some of the light. Hence, less light is reflected back through the properly etched vias. As a result, the under-etched vias appear brighter than the properly etched vias. Therefore, the under-etched vias and properly etched vias can be detected and identified based on the contrast of light reflecting back through the vias. The process then terminates in step 306.

Figure 4:
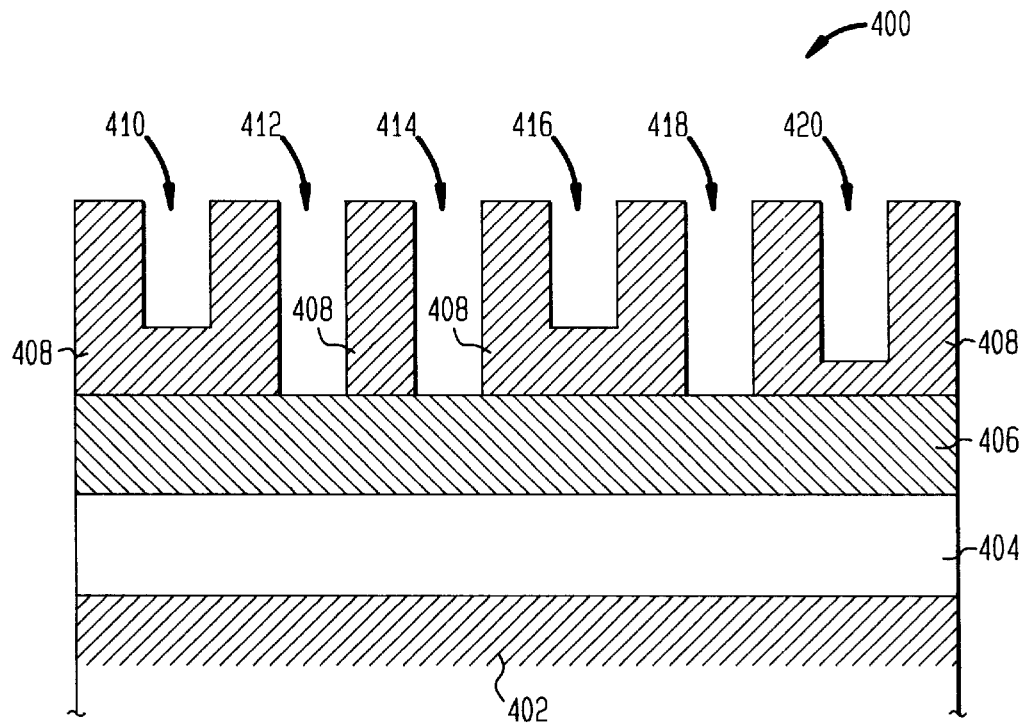
FIG. 4 illustrates a cross section of an exemplary silicon wafer stack including a wafer, a metal/oxide layer, a dielectric layer, and a metal layer having a plurality of spaces.

In another embodiment, the present invention detects under-etched spaces (e.g., line spaces) in a metal layer in a wafer stack comprising the metal layer disposed on an oxide layer. To facilitate discussion, FIG. 4 illustrates a cross section of an exemplary silicon wafer stack 400 including a wafer 402, a metal/oxide layer 404, a dielectric layer 406, and a metal layer 408. Metal layer 408 includes a plurality of spaces 410, 412, 414, 416, 418, and 420, which may be etched on metal layer 408 using well known conventional etching processes such as metal reactive ion etching (RIE) process.

One of the main uses of the spaces (e.g., line spaces) in metal layer 408 is to electrically isolate a metal layer portion from a neighboring metal layer portion. For example, spaces 412 and 414 define an isolated metal layer portion between them and can thus be used to electrically isolate a metal layer portion from its neighboring metal layer portions. In addition, the spaces in metal layer 408 may also be employed to provide connections between any of the layers and a layer which may subsequently be deposited above metal layer 408 through vias.

The spaces in FIG. 4 can be classified into two categories. First, due to the presence of metal underneath, spaces 410, 416, and 420 do not come in direct contact with dielectric layer 406 and are thus referred to as "under-etched" line spaces. On the other hand, spaces 412, 414, and 418 are properly etched because they have been etched completely through metal layer 408 so as to come in contact with oxide layer 406 underneath.

Those skilled in the art will appreciate that layers 404, 406, and 408 can be disposed on wafer 402 in a different order and that the spaces can be formed on any one of layers 404, 406, and 408. It should also be noted that the silicon wafer layer stack 400 of FIG. 4 is shown for illustration purposes only and other additional layers, which have not been described, may be present above, below, and between the layers shown. These other layers may be used to provide, for example, additional interconnecting layers or layers from which components may be formed. Further, not all of the shown layers need necessarily be present and some or all may be substituted by other different layers.

In order to detect under-etched spaces in wafer stack 400, the present invention etches dielectric layer 406 underneath the properly-etched spaces without substantially etching the under-etched spaces. Specifically, wafer stack 400 including the spaces is exposed to an etchant. The etchant is preferably chosen to have high selectivity of dielectric layer 406 to metal layer 408 so that the etchant etches dielectric layer 406 at a substantially faster rate than metal layer 408.

During the etching process, properly-etched spaces 412, 414, and 418 allow the etchant to come in direct contact with dielectric layer 406 and thereby enable the etchant to etch grooves or cavities in dielectric layer 406. In contrast, metal layer 408 directly below under-etched spaces 410, 416, and 420 may form a barrier to the etchant so that the etchant is inhibited from reaching dielectric layer 406 underneath metal layer 408. Wafer stack 400 is thus exposed to the etchant until dielectric layer 406 underneath properly-etched vias 412, 414, and 418 has been etched to a desired thickness. After the etching process, the wafer stack may be cleaned and/or dried.

In the present embodiment, the metal for metal layer 408 may be any of the aforementioned metals suitable for use with metal layer 206 of FIG. 2. Likewise, the dielectric material for dielectric layer 406 may be any of the dielectric material suitable for use with dielectric layer 208 of FIG. 2. Suitable etchants that can selectively etch these dielectric materials without substantially etching the metals are well known in the art and include, for example, hydrofluoric acid (HF) and HF-based solutions.

The preferred etching method of the present invention is a wet etching process where the wafer stack is exposed, for example by dipping or bathing, to an etching solution. Even though the preferred etching technique is wet etching, those skilled in the art will recognize that other etching techniques that can selectively etch the metal layer can be used such as dry etching, plasma etching, etc.

Figure 5:
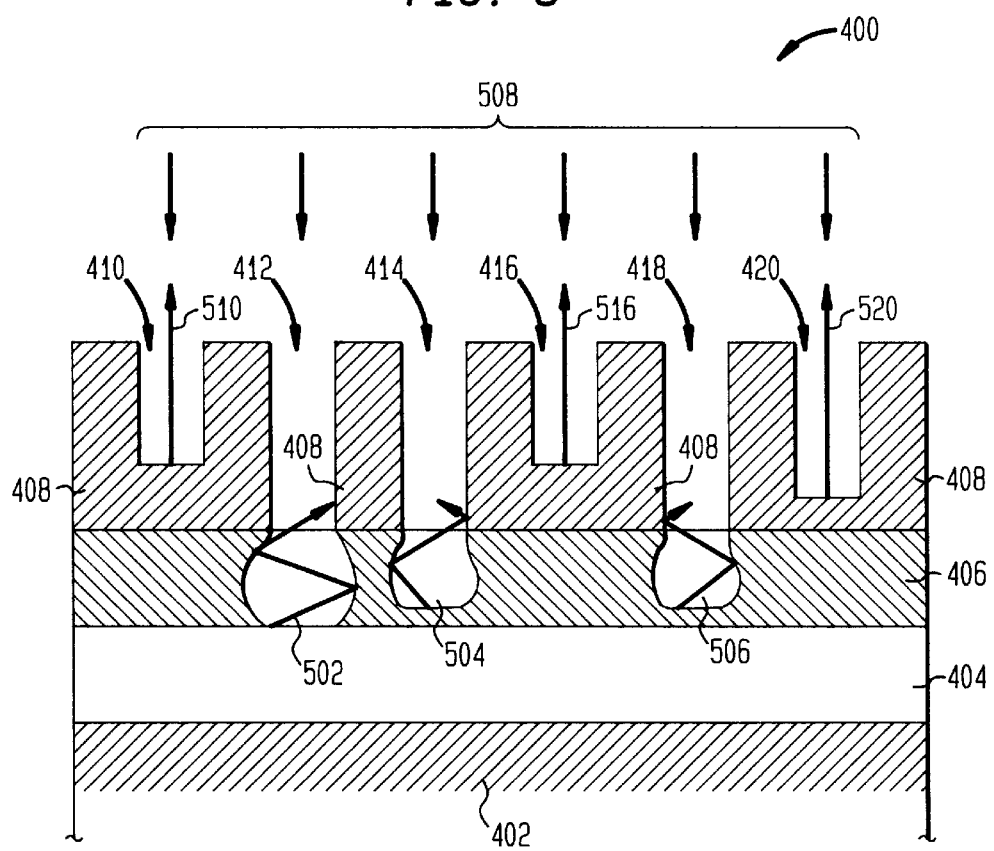
FIG. 5 illustrates in accordance with one aspect of the present invention a cross section of the wafer stack after being exposed to an etchant chosen to have high selectivity of dielectric layer to metal layer.

FIG. 5 illustrates a cross section of wafer stack 400 after being exposed to an etchant chosen to have a high selectivity of dielectric layer 406 to conductive layer 408. The selected etchant etches grooves or cavities 502, 504, and 506 in dielectric layer 406 under properly-etched line spaces 412, 414, and 418, respectively. In contrast, metal layer 408 inhibits the etchant from etching dielectric layer 406 underneath under-etched spaces 410, 416, and 420. Hence, holes or cavities typically are not formed in dielectric layer 406 directly below under-etched spaces 410, 416, and 420. This enhances the existing contrast between the surface of metal layer 408 over the under-etched spaces and the surface of dielectric layer 406 over the properly-etched spaces.

After the etching process, wafer stack 400 is optically inspected to detect and identify under-etched spaces and properly-etched spaces. When the spaces of wafer stack 400 are exposed to light 508, the walls defining grooves or cavities 502, 504, and 506 etched in dielectric layer 406 may scatter incoming light 508. Moreover, some light may pass through the walls of holes or cavities 502, 504, and 506. As a result, less light is reflected back out through properly-etched spaces 412, 414, and 418. In contrast, metal layer 408 at the bottom of under-etched spaces 410, 416, and 420 reflect back much of the light 508 through the spaces. Hence, more light can be reflected back through under-etched spaces 410, 416, and 420 than through properly-etched spaces 412, 414, and 418. Accordingly, under-etched spaces 410, 416, and 420 appear brighter than properly etched spaces 412, 414, and 418 when exposed to light 508. In this manner, the under-etched spaces and properly etched spaces can be detected and identified based on the contrast of light reflecting back through the spaces.

Figure 6:
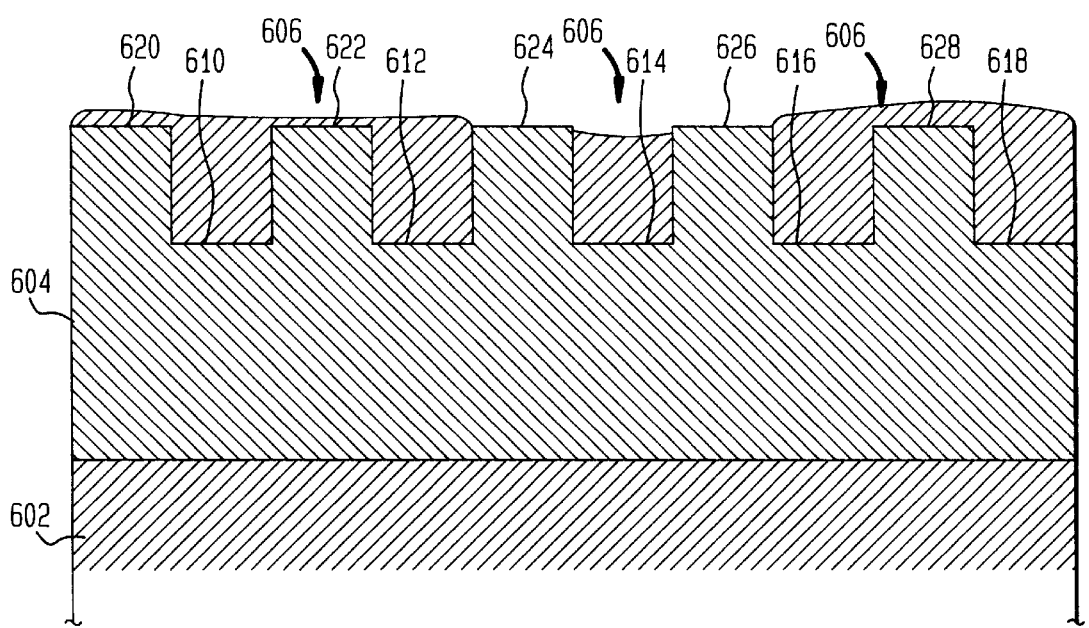
FIG. 6 illustrates a cross section of a silicon wafer stack comprising a polished metal layer over a dielectric layer.

In yet another embodiment, the present invention detects under-polished metal layer portions over a damascene dielectric layer structure in a wafer stack. The metal layer may be deposited over the damascene dielectric layer structure using a suitable deposition process and thereafter polishing off the portion above the dielectric layer using a chemical-mechanical polish (CMP) process. To facilitate discussion, FIG. 6 illustrates a cross section of a silicon wafer stack 600 comprising a metal layer 606 deposited and polished over a dielectric layer 604 on a wafer 602. The structure of dielectric layer 604 comprises a plurality of grooved portions 610, 612, 614, 616, and 618 and a plurality of raised portions 620, 622, 624, 626, and 628 defined by the sides or walls of dielectric layer 604.

With reference to FIG. 6, the surface of metal layer 606 has been polished using CMP process to polish off metal layer 606 so as to be substantially even with the surface of raised portions 620, 622, 624, 626, and 628 of dielectric layer 604. Often however, metal CMP may not polish off all metal residues evenly over the raised portions 620, 622, 624, 626, and 628 of dielectric layer 604 structure. For example, portions of metal layer 606 over the top surface defined by raised portions 620, 622, 624, 626, and 628 of dielectric layer 604 have not been polished off by the CMP process. Accordingly, metal layer 606 portions over dielectric layer 604 portions 610, 612, 616, 618, 620, 622, and 628 are referred to as under-polished metal layer 606 portions. Under-polished metal layer portions may create unintended electrical shorts among adjacent metal features.

In contrast, metal layer 606 over portions 614, 624, and 626 of dielectric layer 604 structure has been properly polished off. That is, the top surface of metal layer portions over portions 614, 624 and 626 are substantially even with the surface of raised portions 624 and 626. Raised portions 624 and 626 are referred to as properly-polished dielectric layer portions. Properly-polished dielectric layer portions 624 and 626 facilitate isolation of metal layer portion 614 from neighboring metal layer portions and thereby ensuring proper electrical isolation.

In order to detect and identify under-polished metal layer portions in wafer stack 600, the present invention etches dielectric layer 604 without substantially etching metal layer 606 to enhance contrast between the under-polished and properly-polished portions. In particular, wafer stack 600 including the properly-polished dielectric layer is exposed to an etchant. The etchant is preferably chosen to have high selectivity of dielectric layer 604 to metal layer 606 so that the etchant etches dielectric layer 604 at a substantially faster rate than metal layer 606.

During the etching process, the etchant comes in direct contact with properly-polished dielectric layer portions 624 and 626 of dielectric layer 604 and thereby etch grooves or cavities in dielectric layer 604. In contrast, under-polished metal layer 606 portions over dielectric layer 604 portions 610, 612, 616, 618, 620, 622, and 628 are etched at a substantially slower rate so that the etchant is substantially inhibited from reaching dielectric layer 604 underneath under-polished metal layer 606 portions 620, 622, and 628. Wafer stack 600 is exposed to the etchant in this manner until dielectric layer 604 underneath properly-polished portions 624 and 626 has been etched to a desired thickness. After the etching process, the wafer stack may be cleaned and/or dried.

In the present embodiment, the metal for the metal layer 606 may be any of the aforementioned metals suitable for use with metal layer 206 of FIG. 2. Likewise, the dielectric material for dielectric layer 406 may be any of the dielectric material suitable for use with dielectric layer 208 of FIG. 2. Similarly, etchants that can selectively etch these dielectric materials without substantially etching the metals may be any of the etchants suitable for use with metal layer 408 and dielectric layer 406 of FIGS. 4 and 5.

The preferred etching method of the present invention is wet etching process where the wafer stack is exposed, for example by dipping or bathing, to an etching solution. Even though the preferred etching technique is wet etching, those skilled in the art will recognize that other etching techniques that can selectively etch the metal layer can be used such as dry etching, plasma etching, etc.

Figure 7:
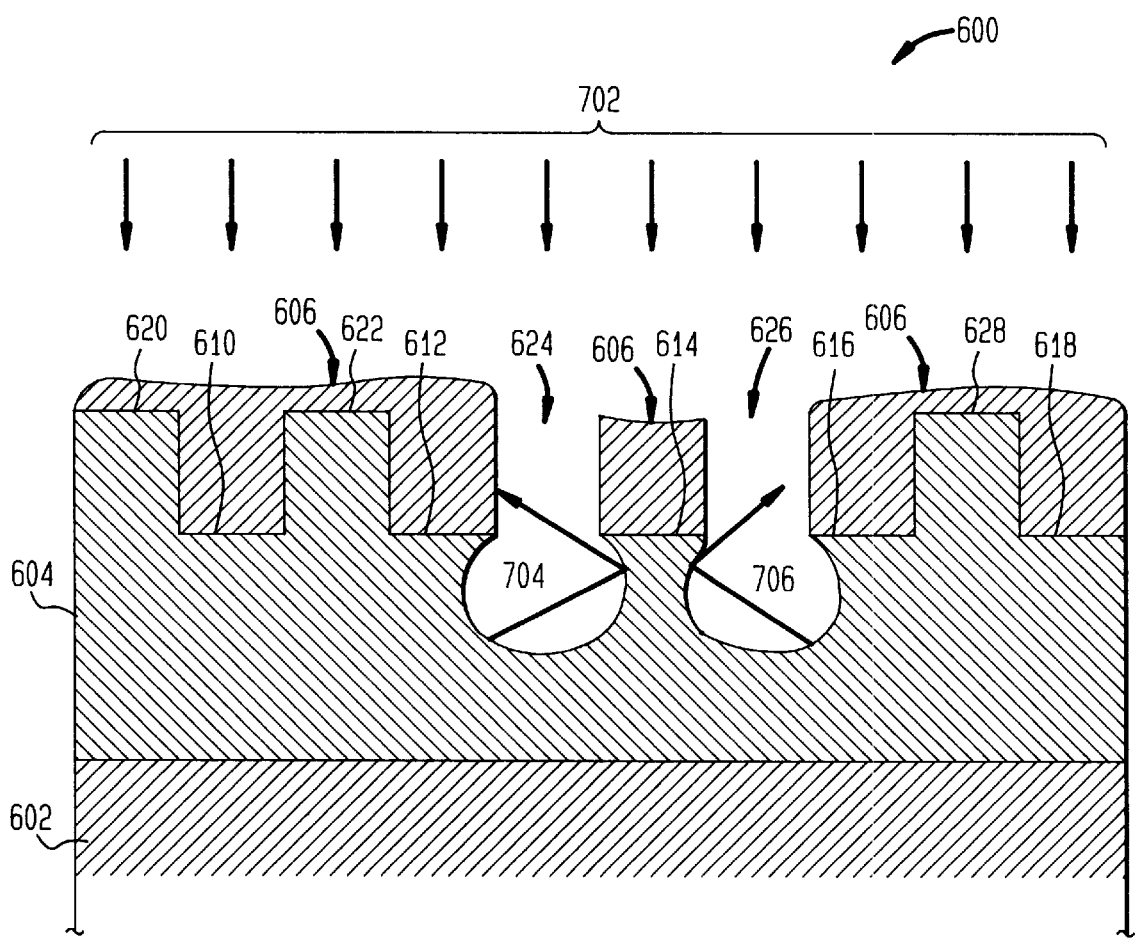
FIG. 7 illustrates in accordance with one embodiment of the present invention a cross section of the wafer stack after being exposed to an etchant chosen to have high selectivity of dielectric layer to metal layer.

FIG. 7 illustrates a cross section of wafer stack 600 after being exposed to the etchant chosen to have high selectivity of dielectric layer 604 to metal layer 606. The selected etchant etches grooves or cavities 704 and 706 in dielectric layer 604 under properly-polished dielectric layer 604 portions 624 and 626, respectively. In contrast, metal layer 606 substantially inhibits the etchant from etching dielectric layer 604 portions 610, 612, 616, 618, 620, 622, and 628 underneath under-polished metal layer 606 portions. Thus in general, grooves or cavities are not formed in dielectric layer 406 directly below under-polished metal layer 606.

After the etching process, wafer stack 600 is optically inspected to detect and identify under-polished metal layer portions and properly-polished dielectric layer portions. When wafer stack 600 is exposed to light 702, the walls defining grooves or cavities 704 and 706 etched in dielectric layer 604 scatters some incoming light 702. Furthermore, some light 702 may also pass through the walls of grooves or cavities 704 and 706. As a result, less light is reflected back out through grooves or cavities 704 and 706 etched in dielectric layer 604.

In contrast, under-polished metal layer 606 portions over under-polished dielectric 606 portions 610, 612, 616, 618, 620, 622, and 628 reflect back much of the light 702. Hence, more light can be reflected back from under-polished metal layer 606 portions than from properly-polished dielectric layer 604 portions. Accordingly, the under-polished metal layer portions appear brighter than the properly-polished dielectric layer portions when exposed to light 702. In this manner, the under-polished metal layer portions and properly-polished dielectric layer portions can be detected and identified based on the contrast of light reflecting back from the surface.

Unlike conventional techniques which limited inspection to a limited area or cross section of a wafer, the embodiments of the present invention allow inspection and detection of the above mentioned features in the entire wafer stack. In addition, the present invention does not require a larger test structure for inspection. Further, unlike conventional methods that require the use of precision needles, the present invention is operationally easy to carry out. Hence, the methods of the present invention save time and expenses while ensuring the accuracy of the inspection result. Additionally, in combination with inspection tools such as KLA 2135 or KLA-Tencor AIT, the yield of chips can be determined immediately after applying the methods of the present invention rather than waiting for the result of electrical tests in conventional techniques.

While this invention has been described in terms of several preferred embodiments, there are alterations, permutations, and equivalents which fall within the scope of this invention. It should also be noted that there are many alternative ways of implementing the methods of the present invention. It is therefore intended that the following appended claims be interpreted as including all such alterations, permutations, and equivalents as falling within the true spirit and scope of the present invention.

What is claimed is:

1. A method for detecting under-etched vias in a wafer stack comprising a dielectric layer disposed on a metal layer, said dielectric layer having a plurality of vias etched therein, said method comprising:

exposing said wafer stack, including said plurality of vias, to an etchant, said etchant being configured to etch said metal layer at a substantially faster rate than said dielectric layer to form cavities in said metal layer below properly-etched vias of said plurality of vias; and optically inspecting said plurality of vias in said wafer stack to detect under-etched vias among said plurality of vias wherein the under-etched vias reflect more light than said cavities etched into said metal layer.

2. The method as recited in claim 1 wherein said optically inspecting step further comprising:

exposing said plurality of vias, including said cavities, in said wafer to light;

viewing said plurality of vias, including said cavities, in said wafer stack; and detecting the under-etched vias.

3. The method as recited in claim 1 wherein said wafer stack is exposed to said etchant in a wet etching process.

4. The method as recited in claim 1 wherein said etchant etches said metal layer through said properly-etched vias of said plurality of vias.

5. The method as recited in claim 1 wherein said cavities etched into said metal layer scatter the light thereby reflecting less light than the under-etched vias.

6. The method as recited in claim 1 wherein the under-etched vias are detected by using an optical microscope.

7. The method as recited in claim 6 wherein said optical microscope compares the light contrast among said plurality of vias to identify the under-etched vias.

8. The method as recited in claim 1 wherein the metal for said metal layer is selected from the group consisting essentially of tungsten (W), aluminum (Al), and copper (Cu).

9. The method as recited in claim 1 wherein said etchant is selected from the group consisting essentially of an HCl-based solution, a NaOH-based solution, a phosphoric-acid based solution, acetic acid, and nitride acid.

10. The method as recited in claim 1 wherein the dielectric material for said dielectric layer is selected from the group consisting essentially of TEOS (undoped silicate glass), BPSG (boron-phosphorous doped silicate glass), PSG (p-doped silicate glass), NSG (n-doped silicate glass), SOG (spin-on-glass), and HSQ (FOX).

11. A method for detecting under-etched spaces in a wafer stack comprising a metal layer disposed on a dielectric layer, said metal layer having a plurality of vias etched therein, said method comprising:

exposing said wafer stack, including said plurality of spaces, to an etchant, said etchant being configured to etch said dielectric layer at a substantially faster rate than said metal layer to form cavities in said dielectric layer below properly-etched spaces of said plurality of spaces; and optically inspecting said plurality of spaces in said wafer stack to detect under-etched spaces among said plurality of spaces wherein the under-etched spaces reflect more light than said cavities etched into said dielectric layer.

12. The method as recited in claim 11 wherein said optically inspecting step further comprising:

exposing said plurality of spaces, including said cavities, in said wafer to light;

viewing said plurality of spaces, including said cavities, in said wafer stack; and detecting the under-etched spaces.

13. The method as recited in claim 11 wherein said wafer stack is exposed to said etchant in a wet etching process.

14. The method as recited in claim 11 wherein said etchant etches said dielectric layer through said properly-etched spaces of said plurality of spaces.

15. The method as recited in claim 11 wherein said cavities etched into said dielectric layer scatter the light thereby reflecting less light than the under-etched spaces.

16. The method as recited in claim 11 wherein the under-etched spaces are detected by using an optical microscope.

17. The method as recited in claim 16 wherein said optical microscope compares the light contrast among said plurality of spaces to identify the under-etched spaces.

18. The method as recited in claim 11 wherein the metal for said metal layer is selected from the group consisting essentially of tungsten (W), aluminum (Al), and copper (Cu).

19. The method as recited in claim 11 wherein said etchant is selected from the group consisting essentially of an HF-based solution.

20. The method as recited in claim 11 wherein the dielectric material for said dielectric layer is selected from the group consisting essentially of TEOS (undoped silicate glass), BPSG (boron-phosphorous doped silicate glass), PSG (p-doped silicate glass), NSG (n-doped silicate glass), SOG (spin-on-glass), and HSQ (FOX).

21. A method for detecting under-polished portions in a wafer stack comprising a polished metal layer disposed over a dielectric layer, said dielectric layer forming a structure having a plurality of portions, said method comprising:

exposing said wafer stack, including said plurality of portions, to an etchant, said etchant being configured to etch said dielectric layer at a substantially faster rate than said metal layer to form cavities in said dielectric layer below properly-polished portions of said plurality of portions; and optically inspecting said plurality of portions in said wafer stack to detect under-polished portions wherein the under-polished portions reflect more light than the cavities etched into said dielectric layer.

22. The method as recited in claim 21 wherein said optically inspecting step further comprising:

exposing said plurality of portions, including said cavities, in said wafer to light;

viewing the plurality of portions, including said cavities, in said wafer stack; and detecting the under-polished portions.

23. The method as recited in claim 21 wherein said wafer stack is exposed to said etchant in a wet etching process.

24. The method as recited in claim 23 wherein the dielectric material for said dielectric layer is selected from the group consisting essentially of TEOS (undoped silicate glass), BPSG (boron-phosphorous doped silicate glass), PSG (p-doped silicate glass), NSG (n-doped silicate glass), SOG (spin-on-glass), and HSQ (FOX).

25. The method as recited in claim 21 wherein said cavities etched into said dielectric layer scatter the light thereby reflecting less light than the under-polished portions.

26. The method as recited in claim 21 wherein the under-polished portions are detected by using an optical microscope.

27. The method as recited in claim 26 wherein said optical microscope compares the light contrast among said plurality of portions to identify the under-polished portions.

28. The method as recited in claim 21 wherein the metal for said metal layer is selected from the group consisting essentially of tungsten (W), aluminum (Al), and copper (Cu).

29. The method as recited in claim 21 wherein said etchant is selected from the group consisting essentially of an HF-based solution.

* * * * *